US012661462B2

(12) United States Patent
Kim et al.

(10) Patent No.: US 12,661,462 B2
(45) Date of Patent: Jun. 23, 2026

(54) INHALER

(71) Applicant: KT&G CORPORATION, Daejeon (KR)

(72) Inventors: Tae Heon Kim, Daejeon (KR); Jae Hyun Kim, Daejeon (KR); Mi Jeong Lee, Daejeon (KR); Yongmi Jung, Daejeon (KR); Eun Mi Jeoung, Daejeon (KR); Seung Kyu Han, Daejeon (KR); Minseok Jeong, Daejeon (KR); Tae Young Chung, Daejeon (KR)

(73) Assignee: KT&G CORPORATION, Daejeon (KR)

( * ) Notice: Subject to any disclaimer, the term of this patent is extended or adjusted under 35 U.S.C. 154(b) by 555 days.

(21) Appl. No.: 18/269,664

(22) PCT Filed: Mar. 20, 2023

(86) PCT No.: PCT/KR2023/003636
§ 371 (c)(1),
(2) Date: Jun. 26, 2023

(87) PCT Pub. No.: WO2023/229175
PCT Pub. Date: Nov. 30, 2023

(65) Prior Publication Data
US 2024/0374846 A1 Nov. 14, 2024

(30) Foreign Application Priority Data
May 24, 2022 (KR) ........................ 10-2022-0063549

(51) Int. Cl.
*A61M 15/00* (2006.01)
(52) U.S. Cl.
CPC ...... *A61M 15/0013* (2014.02); *A61M 15/009* (2013.01); *A61M 15/0095* (2014.02)

(58) Field of Classification Search
CPC ............ A61M 15/0013; A61M 15/009; A61M 15/0095; A61M 15/007; A61M 2209/045;
(Continued)

(56) References Cited

U.S. PATENT DOCUMENTS

| | | | | | |
|---|---|---|---|---|---|
| 3,605,738 | A | * | 9/1971 | Ciranna ............ | A61M 15/0065 |
| | | | | | 239/350 |
| 4,393,884 | A | * | 7/1983 | Jacobs .............. | A61M 15/0093 |
| | | | | | 131/273 |

(Continued)

FOREIGN PATENT DOCUMENTS

| | | |
|---|---|---|
| CN | 102470226 A | 5/2012 |
| CN | 103547791 A | 1/2014 |

(Continued)

OTHER PUBLICATIONS

Korean Office Action dated Apr. 19, 2024 in Application No. 10-2022-0063549.
(Continued)

*Primary Examiner* — Victoria Murphy
(74) *Attorney, Agent, or Firm* — Sughrue Mion, PLLC

(57) ABSTRACT

An inhaler includes a housing having one surface, the other surface opposite to the one surface, and a plurality of side surfaces connecting the one surface and the other surface, a mouthpiece which is disposed on the one side of the housing, a reservoir which is disposed inside the housing and stores an inhalable composition, a nozzle which extends from the mouthpiece to the reservoir, and a needle valve which is movably disposed inside the nozzle, when a suction force is not applied to the mouthpiece, the needle valve is maintained in a first state in which the nozzle is closed, and when a suction force is applied through the mouthpiece, the needle valve is switched into a second state in which the nozzle is opened.

13 Claims, 4 Drawing Sheets

(58) Field of Classification Search
CPC . A61M 15/0093; A61M 11/001; A61M 11/02
See application file for complete search history.

(56)                          References Cited

U.S. PATENT DOCUMENTS

| | | | | | |
|---|---|---|---|---|---|
| 4,576,157 | A | * | 3/1986 | Raghuprasad | .... A61M 15/0091 |
| | | | | | 128/200.23 |
| 6,170,482 | B1 | | 1/2001 | Howlett | |

FOREIGN PATENT DOCUMENTS

| | | | | |
|---|---|---|---|---|
| CN | 106535676 | A | 3/2017 | |
| JP | 9-322938 | A | 12/1997 | |
| JP | 2009-131367 | A | 6/2009 | |
| KR | 10-2003-0028737 | A | 4/2003 | |
| KR | 20-0438243 | Y1 | 2/2008 | |
| KR | 10-2012-0037938 | A | 4/2012 | |
| KR | 10-2012-0129977 | A | 11/2012 | |
| KR | 10-1759972 | B1 | 7/2017 | |
| KR | 10-1994554 | B1 | 6/2019 | |
| WO | 87/04354 | A1 | 7/1987 | |
| WO | WO-9013335 | A1 | * 11/1990 | ........ A61M 15/0091 |

OTHER PUBLICATIONS

Extended European Search Report dated May 24, 2024 in Application No. 23725943.7.
Communication dated Mar. 20, 2026, in Chinese Application No. 202380009694.2.

* cited by examiner

INHALER

CROSS REFERENCE TO RELATED APPLICATIONS

This application is a National Stage of International Application No. PCT/KR2023/003636 filed on Mar. 20, 2023, claiming priority based on Korean Patent Application No. 10-2022-0063549 filed on May 24, 2022.

TECHNICAL FIELD

An inhaler is disclosed.

BACKGROUND ART

In general, an inhaler is a device used to inhale a composition such as a medicine through the oral cavity or nasal cavity as a liquid or gas in the process of inhalation. Such an inhaler includes a container for accommodating an inhalable composition, and the composition is sprayed from the container through a thin tube to the oral cavity or nasal cavity through an intake to be finally inhaled by a user.

The above description has been possessed or acquired by the inventor(s) in the course of conceiving the present disclosure and is not necessarily an art publicly known before the present application is filed.

Prior Document: Korean Patent Gazette No. 10-1759972

DISCLOSURE OF THE INVENTION

Technical Goals

An object according to an embodiment is to provide an inhaler including a valve that operates to open and close a nozzle by moving up and down in conjunction with a suction force so that an inhalable composition is sprayed when a user applies the suction force, and an spraying amount is adjusted so that an inhalable composition with fine particles is sprayed during the spraying.

The technical tasks obtainable from the present disclosure are non-limited by the above-mentioned technical tasks. And, other unmentioned technical tasks can be clearly understood from the following description by those having ordinary skill in the technical field to which the present disclosure pertains.

Technical Solutions

According to an aspect for achieving the above object, an inhaler includes a housing having one surface, the other surface opposite to the one surface, and a plurality of side surfaces connecting the one surface and the other surface, a mouthpiece which is disposed on the one side of the housing, a reservoir which is disposed inside the housing and stores an inhalable composition, a nozzle which extends from the mouthpiece to the reservoir, and a needle valve which is movably disposed inside the nozzle. When a suction force is not applied to the mouthpiece, the needle valve is maintained in a first state in which the nozzle is closed. When a suction force is applied through the mouthpiece, the needle valve is switched into a second state in which the nozzle is opened.

According to an aspect, the first state may be defined as a state in which the needle valve comes into contact with the nozzle, and the second state may be defined as a state in which the needle valve does not come into contact with the nozzle.

According to an aspect, the inhaler may further include a piston which has one surface coupled to the needle valve, and vertically reciprocates in a first direction from the other surface to the one surface of the housing or a second direction from the one surface to the other surface of the housing, and a spring which is provided below the piston in a preloaded state. When a suction force is not applied to the mouthpiece, the spring may push the piston up in the first direction to maintain the first state. When a suction force is applied through the mouthpiece, the piston may overcome preload of the spring and move in the second direction to switch the state into the second state.

According to an aspect, the inhaler may further include a passage which is formed inside the housing and extends from one side of the mouthpiece to a bottom portion of the piston, and the passage may transfer a suction force applied to the mouthpiece to the piston.

According to an aspect, the inhaler may further include a negative pressure forming portion which forms a space between the piston and the passage, and the negative pressure forming portion may induce the piston to move in the second direction by generating a negative pressure by the suction force.

According to an aspect, the nozzle may include a first nozzle portion adjacent to the mouthpiece, and a second nozzle portion adjacent to the reservoir, and the first nozzle portion may be formed to have a diameter smaller than a diameter of the second nozzle portion.

According to an aspect, the needle valve may include a first valve portion which is formed on a front end and vertically reciprocates in a first direction from the other surface to the one surface of the housing or a second direction from the one surface to the other surface of the housing through the first nozzle portion and the second nozzle portion, and a second valve portion which is formed on a lower portion of the first valve portion, and the first valve portion may be formed to have a diameter smaller than a diameter of the second valve portion.

According to an aspect, the first valve portion may be formed to have the diameter smaller than the diameter of the first nozzle portion.

According to an aspect, the first valve portion may not come into contact with the nozzle in the first state or the second state, and the second valve portion may come into contact with the nozzle in the first state and may not come into contact with the nozzle in the second state.

According to an aspect, the nozzle may further include a sealing member provided in the second nozzle portion, and the second valve portion may come into contact with the sealing member in the first state, and may not come into contact with the sealing member by moving in the second direction in the second state.

According to an aspect, a first gap formed between the first valve portion and the first nozzle portion may be smaller than a second gap formed between the first valve portion and the sealing member.

According to an aspect, the first gap may be formed in the first state or the second state, and the second gap may be formed in the second state.

According to an aspect, the second gap may allow movement of an inhalable composition discharged from the reservoir, and the first gap may allow the movement of the inhalable composition to the mouthpiece by controlling a particle size of the inhalable composition passing through the second gap.

According to an aspect, the first gap is formed to 0.015 millimeters (mm) to 0.03 mm.

Effects

According to the inhaler according to an embodiment, a valve which operates to open and close a nozzle by moving up and down in conjunction with a suction force is provided to spray an inhalable composition when a user applies a suction force, thereby adjusting an spraying amount so that the inhalable composition with fine particles is sprayed during the spraying.

The effects of the inhaler are not limited to the above-mentioned effects, and other unmentioned effects can be clearly understood from the above description by those having ordinary skill in the technical field to which the present disclosure pertains.

Figure 1:
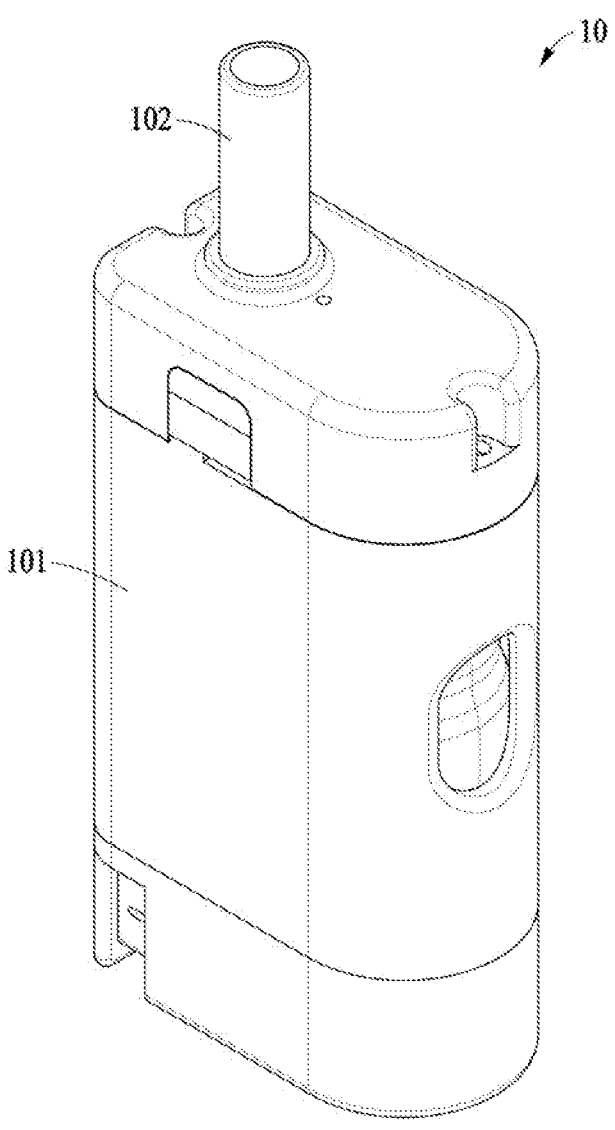
FIG. 1 is a perspective view of an inhaler according to an embodiment.

The accompanying drawings illustrate desired embodiments of the present disclosure and are provided together with the detailed description for better understanding of the technical idea of the present disclosure. Therefore, the present disclosure should not be construed as being limited to the embodiments set forth in the drawings.

BEST MODE FOR CARRYING OUT THE INVENTION

The terminology used herein is for the purpose of describing particular embodiments only and is not to be limiting of the embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the embodiments with reference to the accompanying drawings, like reference numerals refer to like components and a repeated description related thereto will be omitted. In the description of embodiments, detailed description of well-known related structures or functions will be omitted when it is deemed that such description will cause ambiguous interpretation of the present disclosure.

In addition, terms such as first, second, A, B, (a), (b), and the like may be used to describe components of the embodiments. These terms are used only for the purpose of discriminating one constituent element from another constituent element, and the nature, the sequences, or the orders of the constituent elements are not limited by the terms. When one constituent element is described as being "connected", "coupled", or "attached" to another constituent element, it should be understood that one constituent element can be connected or attached directly to another constituent element, and an intervening constituent element can also be "connected", "coupled", or "attached" to the constituent elements.

The same name may be used to describe an element included in the embodiments described above and an element having a common function. Unless otherwise mentioned, the descriptions of the embodiments may be applicable to the following embodiments and thus, duplicated descriptions will be omitted for conciseness.

FIG. 1 is a perspective view of an inhaler 10 according to an embodiment.

Figure 2:
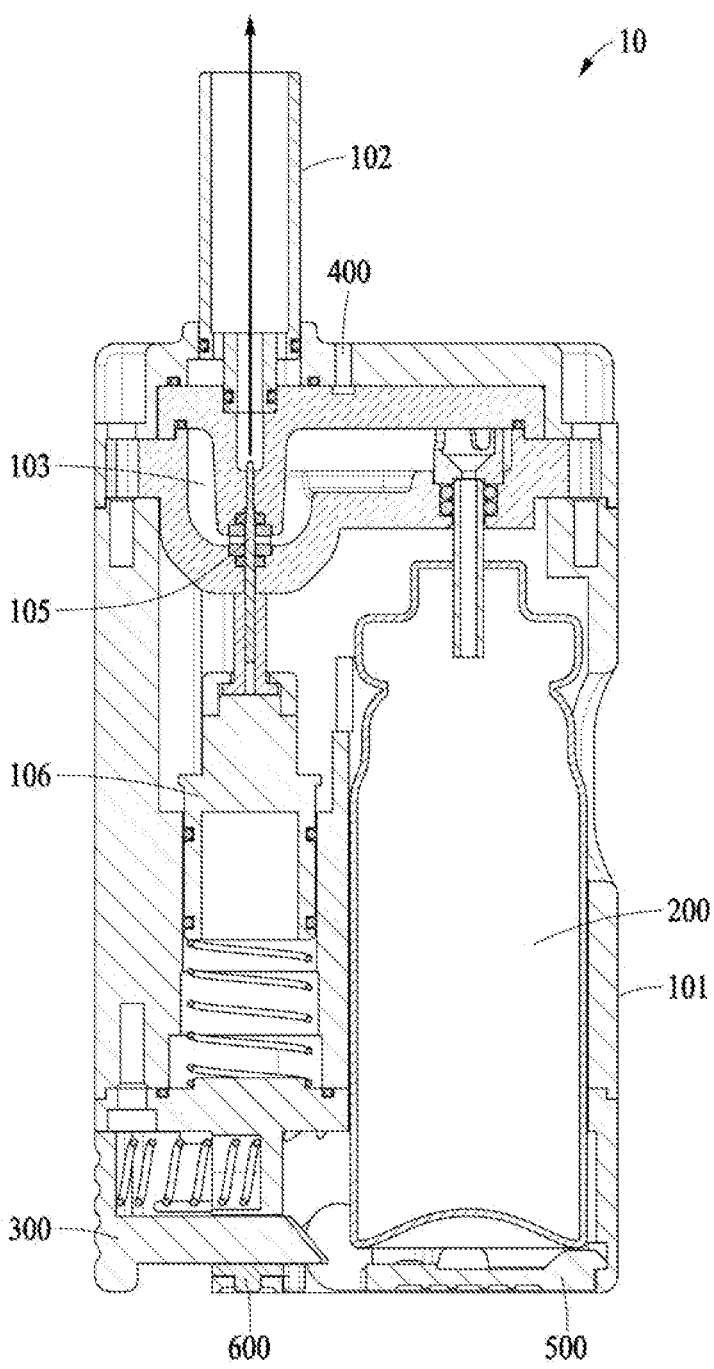
FIG. 2 is a cross-sectional view of an inhaler according to an embodiment.

FIG. 2 is a cross-sectional view of the inhaler 10 according to an embodiment.

Figure 3:
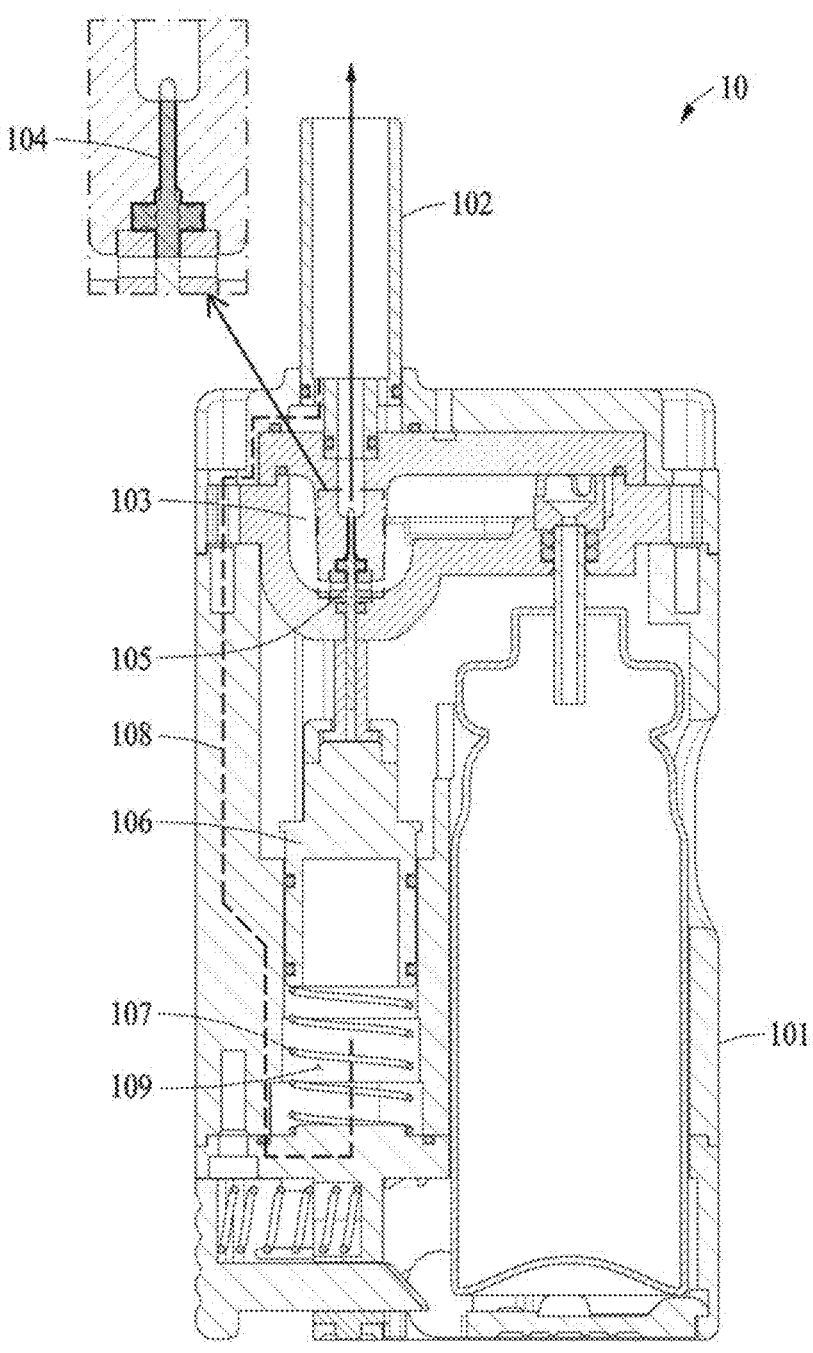
FIG. 3 is a cross-sectional view of an inhaler according to an embodiment.

FIG. 3 is a cross-sectional view of the inhaler 10 according to an embodiment.

FIG. 4 illustrates the inhaler 10 in a first state and a second state.

Referring to FIG. 1, the inhaler 10 according to an embodiment may include a housing 101 and a mouthpiece 102.

The housing 101 may include a first surface formed on one surface, a second surface opposite to the first surface, and a plurality of side surfaces connecting the first surface and the second surface. The first surface of the housing 101 may be, for example, a surface located on the top of the housing 101, and the second surface may be, for example, a bottom surface of the housing 101. Hereinafter, a direction from the second surface to the first surface is defined as a first direction, and a direction from the first surface to the second surface is defined as a second direction.

The mouthpiece 102 may be disposed on the first surface of the housing 101. A user may inhale an inhalable composition accommodated in the inhaler 10 through the mouthpiece 102. At this time, the user may inhale the composition, for example, in the form of an aerosol or in the form of a powder. Hereinafter, the inhaler 10 according to an embodiment will be described using the inhaler 10 that sprays an inhalable composition in the form of an aerosol as an example.

Referring to FIG. 2, in the inhaler 10 according to an embodiment, a canister 200 for accommodating an inhalable composition may be mounted in the housing 101, and a certain amount of the composition of the canister 200 may be filled in a reservoir 103. A user may visually identify a remaining amount of the composition stored in the reservoir 103 through a viewing window (not shown) provided in the housing 101. A filling lever 300 that may be pressurized by a user may be provided to fill the reservoir 103 with the composition accommodated in the canister 200. The filling lever 300 may be provided on the second surface of the housing 101. When a user pressurizes the filling lever 300, the filling lever 300 may push a bottom surface of the canister 200 up in the first direction so that an injection hole of the canister 200 communicates with the reservoir 103, and the composition may move from the canister 200 to the reservoir 103 through the injection hole. In addition, the inhaler 10 according to an embodiment may include a counter (not shown) that counts the number of times of filling in connection with a vertical movement of the canister 200 during the filling of the reservoir 103, and a display window (not shown) that displays a remaining amount of a composition in the canister 200. The composition stored in the reservoir 103 may be sprayed in the form of an aerosol, as a user applies a suction force to the mouthpiece 102. At this time, an inhale interlocking valve 105 that opens and closes the reservoir 103 may be operated by the suction force, and the opening and closing operation of the inhale interlocking valve 105 may be controlled by a piston 106. In addition, the reservoir 103 may be provided with a relief valve (not shown), and a relief vent hole 400 may be provided on the first surface of the housing 101. This relief valve is interlocked with the filling lever 300 through a relief bar (not shown), a relief bar moving projection (not shown), and the like. Therefore, the relief valve may be opened first to discharge a residual gas in the reservoir 103, immediately before the filling lever 300 pushes the canister 200 up in the first direction to fill the reservoir 103. Additionally, the inhaler 10 according to an embodiment may include a cover 500 and a locking device 600 for preventing the detachment of the canister 200.

In the inhaler 10 described above, a needle valve method developed to solve problems that occur when an aerosol is sprayed into the user's nasal cavity or oral cavity is applied to the inside of the housing 101, and this needle valve method will be described in detail below with reference to FIGS. 3 and 4.

In general, when a pinch valve method is applied to an inhaler, a problem of wetting the inside of the user's oral cavity may occur due to too large particles of the aerosol sprayed through a nozzle having a circular cross-sectional area. In addition, since a tip of an injection nozzle is positioned inside the oral cavity, a problem in that the aerosol hits the oral cavity hard during the spraying may occur. In order to solve such problems, a needle valve method is applied in the present disclosure.

Referring to FIG. 3, the inhaler 10 according to an embodiment may further include the reservoir 103, a nozzle 104, and a needle valve 105.

The reservoir 103 may be disposed inside the housing 101. The reservoir 103 may store an inhalable composition.

The nozzle 104 may allow the mouthpiece 102 to communicate with the reservoir 103. The nozzle 104 may be provided as a tube extending from the mouthpiece 102 to the reservoir 103.

The needle valve 105 may be movably disposed inside the nozzle 104. For example, the needle valve 105 may move up and down inside the nozzle 104. The needle valve 105 may open or close the nozzle 104 depending on its position within the nozzle 104. That is, the needle valve 105 may open the nozzle 104 so that the mouthpiece 102 and the reservoir 103 communicate with each other, or may close the nozzle 104 so that the mouthpiece 102 and the reservoir 103 are isolated from each other.

In the needle valve method using the needle valve 105, a cross-sectional area for spraying an aerosol may maintain a donut shape as the needle-shaped valve 105 is positioned in the middle of the nozzle 104. In addition, finer particles may be formed by spraying the aerosol from a narrower section compared to the same injection area, and a phenomenon of hitting or wetting the inside of the oral cavity may be improved, because the nozzle 104 for spraying an aerosol is positioned at a lower tip of the mouthpiece 102 which is far from the oral cavity.

The nozzle 104 may be switched to one of a first state or a second state by the needle valve 105. The first state is a state in which the nozzle 104 is closed, and the second state is a state in which the nozzle 104 is opened. In the first state, the mouthpiece 102 and the reservoir 103 may be isolated from each other. In the second state, the mouthpiece 102 and the reservoir 103 may communicate with each other. That is, in the second state, the inhalable composition stored in the reservoir 103 may be discharged to the mouthpiece 102 through the nozzle 104 as indicated by an arrow.

In addition, the needle valve 105 may operate in association with suction.

Specifically, when a suction force is not applied to the mouthpiece 102, the needle valve 105 may maintain the nozzle 104 in the first state. When a suction force is applied through the mouthpiece 102, the needle valve 105 may move in the second direction to switch the nozzle 104 into the second state.

Referring back to FIG. 3, the inhaler 10 according to an embodiment may further include a piston 106, a spring 107, a passage 108, and a negative pressure forming portion 109.

The piston 106 may be disposed inside the housing 101, and one end of the needle valve 105 may be coupled to one surface of the piston 106. The piston 106 may reciprocate vertically in a cylinder.

The spring 107 may be provided below the piston 106. At this time, the spring 107 may be provided in a preloaded state.

The passage 108 may be formed inside the housing 101. The passage 108 may allow the mouthpiece 102 to communicate with the piston 106. Specifically, one end of the passage 108 may be connected to one side of the mouthpiece 102, and the other end of the passage 108 may be connected to the bottom of the piston 106. At this time, one end of the passage 108 may be connected to the mouthpiece 102 at a position spaced apart from a position where the nozzle 104 is connected to the mouthpiece 102. The passage 108 may transfer a suction force applied to the mouthpiece 102 to the piston 106.

The negative pressure forming portion 109 may be formed between the piston 106 and one end of the passage 108 connected to the piston 106. The negative pressure forming portion 109 may form a space between the piston 106 and the passage 108. When a suction force is applied to the mouthpiece 102, the suction force transferred through the passage 108 may reach the negative pressure forming portion 109, and the negative pressure forming portion 109 may generate a negative pressure. Accordingly, the negative pressure forming portion 109 may induce the piston 106 to move in the second direction.

As a result, when a suction force is not applied to the mouthpiece 102, the spring 107 may push the piston 106 up in the first direction so that the needle valve 105 and the nozzle 104 are maintained in the first state. On the other hand, when a suction force is applied to the mouthpiece 102, the suction force may be transferred to the negative pressure forming portion 109 through the passage 108, and the piston 106 may overcome the preload of the spring 107 by the negative pressure generated by the negative pressure forming portion 109, and move in the second direction. Accordingly, the needle valve 105 may move in the second direction and the nozzle 104 may be switched into the second state.

Referring to FIG. 4, the nozzle 104 and the needle valve 105 in the first and second states will be described in more detail.

Figure 4A:
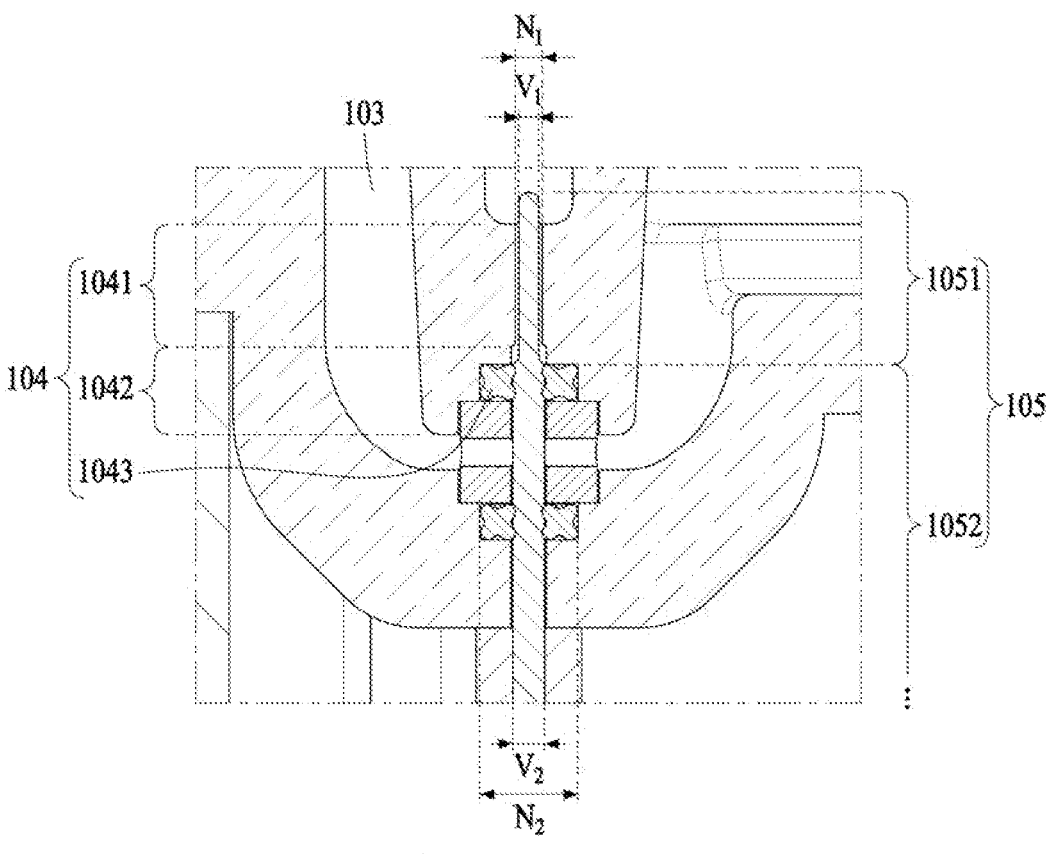
FIG. 4 illustrates an inhaler in a first state and a second state.
Figure 4B:
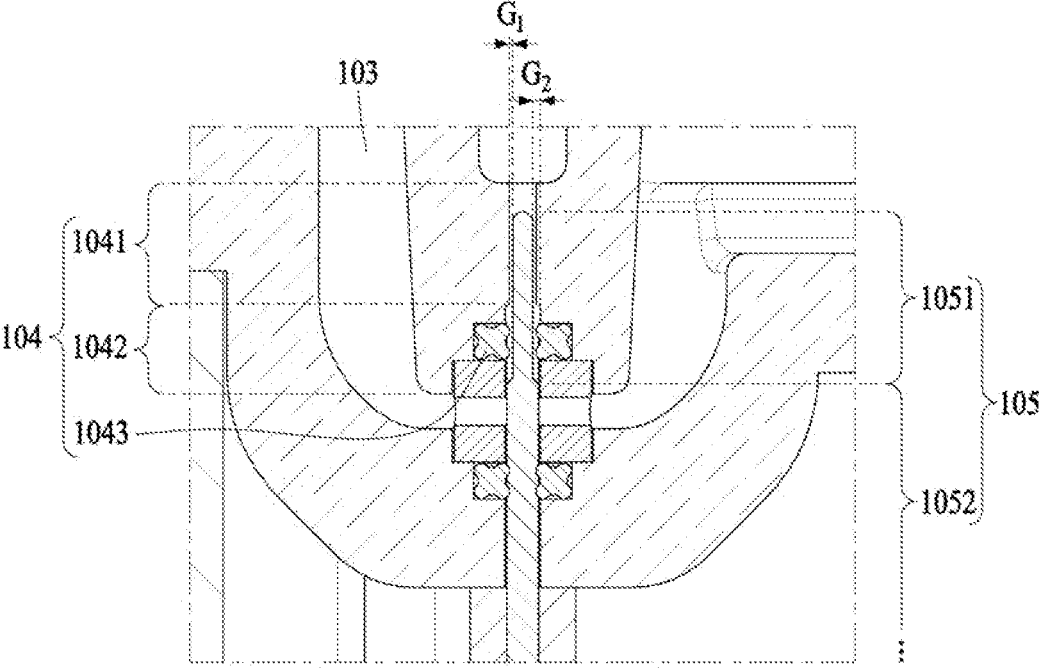

FIG. 4A shows the inhaler 10 in the first state and FIG. 4B shows the inhaler 10 in the second state.

In the first state, the nozzle 104 and the needle valve 105 may come into contact with each other and the mouthpiece 102 and the reservoir 103 may be isolated from each other.

In the second state, the needle valve 105 may move in the second direction so that the nozzle 104 and the needle valve 105 may not come into contact with each other, and the mouthpiece 102 and the reservoir 103 may communicate with each other through the nozzle 104. Accordingly, the inhalable composition in the reservoir 103 may be discharged outside from the reservoir 103 through the mouthpiece 102.

Specifically, the nozzle 104 may include a first nozzle portion 1041 and a second nozzle portion 1042.

The first nozzle portion 1041 may be a portion adjacent to the mouthpiece 102.

The second nozzle portion 1042 may be, for example, a portion located on the bottom of the first nozzle portion 1041 and adjacent to the reservoir 103.

The nozzle 104 may be formed such that the first nozzle portion 1041 has a diameter smaller than that of the second nozzle portion 1042.

The needle valve 105 may include a first valve portion 1051 and a second valve portion 1052.

The first valve portion 1051 may be a portion formed at a front end of the needle valve 105. The first valve portion 1051 may move adjacent to the first nozzle portion 1041 or the second nozzle portion 1042 when the piston 106 moves vertically. For example, in the first state, the first valve portion 1051 may be disposed adjacent to the first nozzle portion 1041. In addition, in the second state, the first valve portion 1051 may move in the second direction to be adjacent to the second nozzle portion 1042.

The second valve portion 1052 may be, for example, a portion formed below the first valve portion 1051. A lower end of the second valve portion 1052 may be coupled to one surface of the piston 106. Accordingly, when the piston 106 vertically reciprocates, the needle valve 105 may vertically reciprocate.

The needle valve 105 may be formed such that the first valve portion 1051 has a diameter smaller than that of the second valve portion 1052.

In addition, the first valve portion 1051 may be formed to have a diameter smaller than that of the first nozzle portion 1041. That is, the first valve portion 1051 may not come into contact with any of the first nozzle portion 1041 and the second nozzle portion 1042 in the first state or the second state.

Meanwhile, the nozzle 104 may further include a sealing member 1043 provided on the second nozzle portion 1042. The sealing member 1043 may be formed of, for example, an O-ring or a Quad-ring composed of an elastic material such as silicon or rubber. An inner diameter of the sealing member 1043 may be larger than the diameter of the first valve portion 1051 and may be equal to or smaller than the diameter of the second valve portion 1052. Also, the inner diameter of the sealing member 1043 may be larger than the diameter of the first nozzle portion 1041.

The second valve portion 1052 may be disposed adjacent to the sealing member 1043 in the first state. That is, in the first state, the second valve portion 1052 may come into contact with the sealing member 1043. Accordingly, the reservoir 103 may be sealed airtightly so that no aerosol leaks through the nozzle 104.

On the other hand, the second valve portion 1052 may move in the second direction with respect to the sealing member 1043 and may not to come into contact with the nozzle 104 in the second state. Accordingly, the inhalable composition stored in the reservoir 103 may be discharged to the mouthpiece 102 through the nozzle 104.

Referring to FIG. 4B, a gap formed between the first nozzle portion 1041 and the first valve portion 1051 is defined as a first gap G1, and a gap formed between the sealing member 1043 and the first valve portion 1051 is defined as a second gap G2. Due to the structure of the nozzle 104 and the needle valve 105 described above, the first gap G1 may be formed to be smaller than the second gap G2.

The first gap G1 may be formed in the first state or the second state. The second gap G2 is formed when the first valve portion 1051 is disposed adjacent to the sealing member 1043, and therefore, the second gap G2 may be formed in the second state in which the needle valve 105 is moved in the second direction.

The second gap G2 may allow the movement of the inhalable composition discharged from the reservoir 103. The first gap G1 may control a particle size of an aerosol which has passed through the second gap G2. That is, since the first gap G1 is smaller than the second gap G2, the first gap G1 may allow only the movement of an aerosol with fine particles from the aerosol. As a result, only an aerosol having a size that is able to pass through the first gap G1 may move to the mouthpiece 102 to be discharged to the user.

That is, when the nozzle 104 is opened by a suction force, the aerosol is finally sprayed to the outside through the first gap G1, but the initial discharge from the reservoir 103 may be performed through the second gap G2 formed between the sealing member 1043 and the first valve portion 1051.

That is, since both the nozzle 104 and the needle valve 105 are formed straight, the first gap G1 is constantly formed regardless of the opening and closing of the nozzle 104, and therefore, the opening and closing is substantially performed by the sealing member 1043 and the needle valve 105.

In this case, the first gap G1 may be formed to have a size of 0.015 millimeters (mm) to 0.03 mm for the spraying of an aerosol with sufficiently small particles. For example, if the size of the first gap G1 is smaller than 0.015 mm, it is difficult for a liquid composition to move along a narrow gap, so that a gas is mainly sprayed, and some liquid droplets may be weakly sprayed as if boiling. On the other hand, if the size of the first gap G1 is larger than 0.03 mm, large liquid droplets are mainly sprayed, which may cause an extremely large spraying amount per unit time, and the user may feel that the nasal cavity or oral cavity is wet. In addition, if the second gap G2 is formed too narrow due to a manufacturing tolerance of the sealing member 1043, a phenomenon which is the same phenomenon occurring due to the narrow first gap G1 may occur, and therefore, in consideration of this point, the second gap G2 may be formed sufficiently larger than the first gap G1. Accordingly, the inhaler 10 according to an embodiment may spray an aerosol with fine particles and easily adjust the spraying amount.

As described above, the inhaler 10 according to an embodiment may maintain a state in which the nozzle 104 is closed by receiving a force of the needle valve 105 normally pushing up in the first direction due to the preload of the spring 107. However, in the inhaler 10 according to an embodiment, when a suction force is applied through the mouthpiece 102 by the user, a negative pressure may be formed on the bottom of the piston 106, the piston 106 may move downward by overcoming the preload of the spring 107, and the needle valve 105 connected to the piston 106 may move downward to form the second gap G2 between the sealing member 1043 and the needle valve 105. Accordingly, the inhalable composition in the reservoir 103 may be discharged to the outside, for example, to the user's oral cavity through the first gap G1 by passing through the second gap G2 in the form of an aerosol. When the user stops inhaling, the piston 106 and the needle valve 105 may move upward again due to a restoring force of the spring 107 and the nozzle 104 may be closed to stop the spraying of the aerosol.

While the embodiments are described with reference to drawings, it will be apparent to one of ordinary skill in the art that various alterations and modifications in form and details may be made in these embodiments without departing from the spirit and scope of the claims and their equivalents. For example, suitable results may be achieved if the described techniques are performed in a different order, and/or if components in a described system, architecture, device, or circuit are combined in a different manner, and/or replaced or supplemented by other components or their equivalents.

Therefore, other implementations, other embodiments, and equivalents to the claims are also within the scope of the following claims.

The invention claimed is:

1. An inhaler comprising:
a housing having one surface, an other surface opposite to the one surface, and a plurality of side surfaces connecting the one surface and the other surface;
a mouthpiece which is disposed on the one surface of the housing;
a reservoir which is disposed inside the housing and stores an inhalable composition;
a nozzle which extends from the reservoir towards the mouthpiece;
a needle valve which is movably disposed inside the nozzle;
a piston which has one surface coupled to the needle valve, and vertically reciprocates in a first direction from the other surface to the one surface of the housing or a second direction from the one surface of the housing to the other surface of the housing; and
a spring which is provided below the piston in a preloaded state,
wherein, when a suction force is not applied to the mouthpiece, the needle valve is maintained in a first state in which the nozzle is closed,
wherein, when the suction force is applied through the mouthpiece, the needle valve is switched into a second state in which the nozzle is opened,
wherein, when the suction force is not applied to the mouthpiece, the spring pushes the piston up in the first direction to maintain the first state, and
wherein, when the suction force is applied through the mouthpiece, the piston overcomes preload of the spring and moves in the second direction to switch into the second state.

2. The inhaler of claim 1,
wherein the first state is defined as a state in which the needle valve comes into contact with the nozzle, and
wherein the second state is defined as a state in which the needle valve does not come into contact with the nozzle.

3. The inhaler of claim 1, further comprising:
a passage which is formed inside the housing and extends from one side of the mouthpiece to a bottom portion of the piston,
wherein the passage transfers the suction force applied to the mouthpiece to the piston.

4. The inhaler of claim 3, further comprising:
a negative pressure forming portion which forms a space between the piston and the passage,
wherein the negative pressure forming portion induces the piston to move in the second direction by generating a negative pressure by the suction force.

5. The inhaler of claim 1,
wherein the nozzle comprises:
a first nozzle portion adjacent to the mouthpiece; and
a second nozzle portion adjacent to the reservoir, and
wherein the first nozzle portion is formed to have a diameter smaller than a diameter of the second nozzle portion.

6. The inhaler of claim 5,
wherein the needle valve comprises:
a first valve portion which is formed on a front end and vertically reciprocates in the first direction from the other surface to the one surface of the housing or the second direction from the one surface of the housing to the other surface of the housing through the first nozzle portion and the second nozzle portion; and
a second valve portion which is formed on a lower portion of the first valve portion,
wherein the first valve portion is formed to have a diameter smaller than a diameter of the second valve portion.

7. The inhaler of claim 6, wherein the first valve portion is formed to have the diameter smaller than the diameter of the first nozzle portion.

8. The inhaler of claim 6,
wherein the first valve portion does not come into contact with the nozzle in the first state or the second state, and
wherein the second valve portion comes into contact with the nozzle in the first state and does not come into contact with the nozzle in the second state.

9. The inhaler of claim 6,
wherein the nozzle further comprises a sealing member provided in the second nozzle portion, and
wherein the second valve portion comes into contact with the sealing member in the first state, and does not come into contact with the sealing member by moving in the second direction in the second state.

10. The inhaler of claim 9, wherein a first gap formed between the first valve portion and the first nozzle portion is smaller than a second gap formed between the first valve portion and the sealing member.

11. The inhaler of claim 10,
wherein the first gap is formed in the first state or the second state, and
wherein the second gap is formed in the second state.

12. The inhaler of claim 10,
wherein the second gap allows movement of the inhalable composition discharged from the reservoir, and
wherein the first gap allows the movement of the inhalable composition to the mouthpiece by controlling a particle size of the inhalable composition passing through the second gap.

13. The inhaler of claim 10, wherein the first gap is formed to be 0.015 mm to 0.03 mm.

* * * * *